US00PP32838P2

(12) United States Plant Patent
Monte-Michielsen

(10) Patent No.: US PP32,838 P2
(45) Date of Patent: Feb. 23, 2021

(54) GERANIUM PLANT NAMED 'TOSDYNDREDI'

(50) Latin Name: ***Pelargonium* Interspecific**
Varietal Denomination: Tosdyndredi

(71) Applicant: Ball Horticultural Company, West Chicago, IL (US)

(72) Inventor: Fabienne Monte-Michielsen, Brielle (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/879,672

(22) Filed: May 20, 2020

(51) Int. Cl.
*A01H 5/02* (2018.01)
*A01H 6/42* (2018.01)

(52) U.S. Cl.
USPC ..... Plt./330

(58) Field of Classification Search
USPC ..... Plt./324, 325, 330
See application file for complete search history.

*Primary Examiner* — Susan McCormick Ewoldt
(74) *Attorney, Agent, or Firm* — Audrey Charles

(57) ABSTRACT

A new and distinct cultivar of Geranium plant named 'Tosdyndredi', characterized by its semi-double type, dark red colored flowers, medium green-colored foliage with faint zonation, and vigorous, upright-mounded growth habit, is disclosed.

1 Drawing Sheet

Latin name of genus and species of plant claimed: *Pelargonium* Interspecific.

Variety denomination: 'Tosdyndredi'.

BACKGROUND OF THE INVENTION

The present invention relates to a new and distinct cultivar of Geranium plant botanically known as *Pelargonium* Interspecific and hereinafter referred to by the cultivar name 'Tosdyndredi'.

The new cultivar originated in a controlled breeding program in Hendrik-Ido-Ambacht, the Netherlands during July 2016. The objective of the breeding program was the development of Geranium cultivars with semi-double type flowers having attractive flower coloration, and a vigorous, upright-mounded growth habit.

The new Geranium cultivar is the result of cross-pollination. The female (seed) parent of the new cultivar is the proprietary *Pelargonium* x *hortorum* breeding selection coded 17-3028, not patented, characterized by its double type, medium red-colored flowers, medium green-colored foliage with zonation, low growth vigor and an upright-mounded growth habit. The male (pollen) parent of the new cultivar is 'Xtreme Night', not patented, characterized by its semi-double type, medium burgundy-colored flowers, medium green-colored foliage with zonation, and moderately vigorous, upright-mounded growth habit. The new cultivar was selected as a single flowering plant within the progeny of the above stated cross-pollination during September 2017 in a controlled environment in Hendrik-Ido-Ambacht, the Netherlands.

Asexual reproduction of the new cultivar by terminal stem cuttings since September 2017 in Hendrik-Ido-Ambacht, the Netherlands and Arroyo Grande, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Tosdyndredi' as a new and distinct cultivar of Geranium plant:

1. Semi-double type, dark red colored flowers;
2. Medium green-colored foliage with faint zonation; and
3. Vigorous, upright-mounded growth habit.

Plants of the new cultivar differ from plants of the female parent primarily in having a darker shade of red-colored flowers and has a more vigorous growth habit. Plants of the new cultivar differ from plants of the male parent primarily in having a lighter shade of red-colored flowers and more branches per plant.

Of the many commercially available Geranium cultivars, the most similar in comparison to the new cultivar is CALLIOPE Large Dark Red 'Amri Trared', U.S. Plant Pat. No. 20,245. However, in comparison, plants of the new cultivar differ from plants of 'Amri Trared' in at least the following characteristics:

1. Plants of the new cultivar have darker red-colored flowers than plants of 'Amri Trared'; and
2. Plants of the new cultivar have smaller diameter flowers than plants of 'Amri Trared'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Tosdyndredi'. The approximately 13-week-old plants were grown in 4.5-inch pots for approximately 9 weeks in a greenhouse in West Chicago, Ill. Plants were given one pinch two weeks before transplant.

DETAILED BOTANICAL DESCRIPTION

Figure 1:
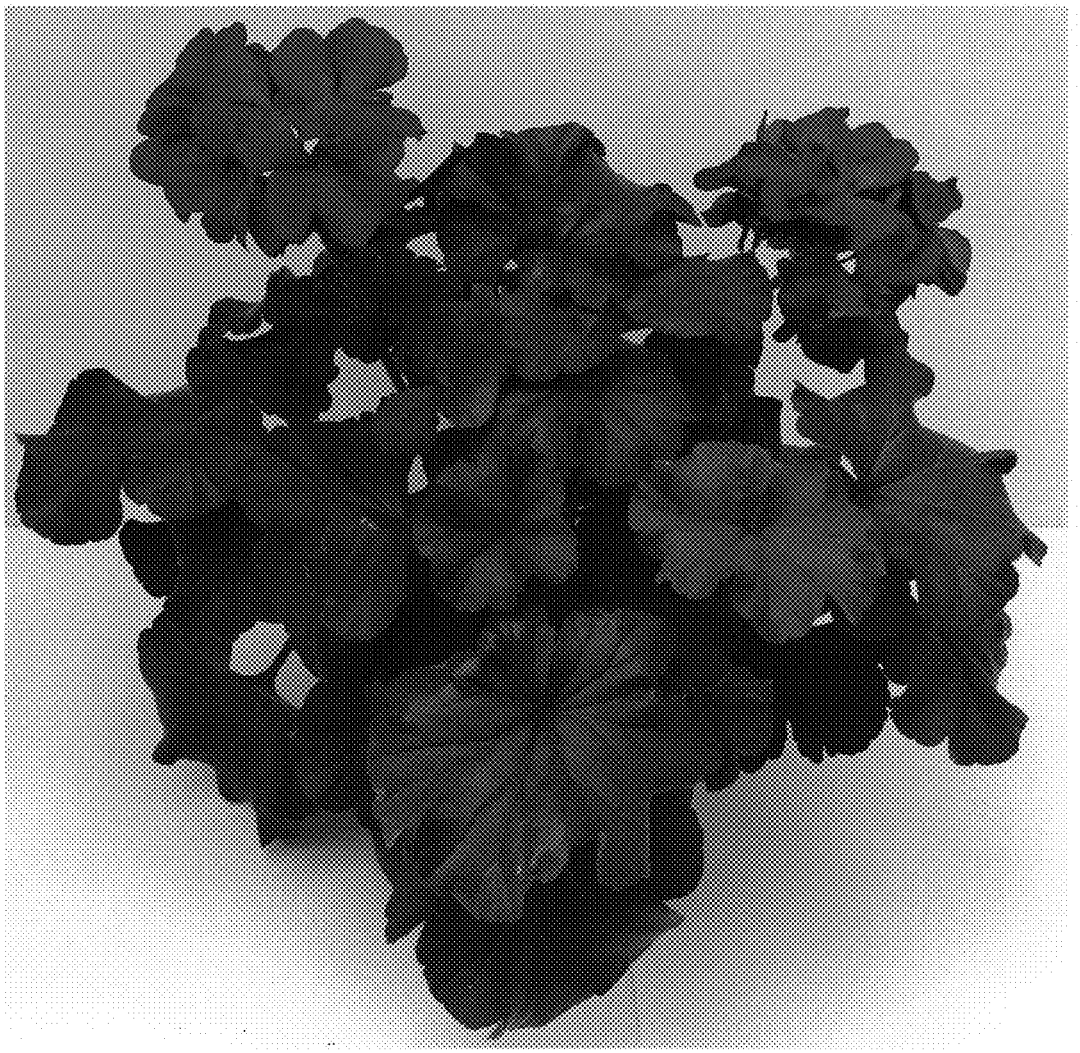
FIG. 1 illustrates a side view of the overall growth and flowering habit of 'Tosdyndredi'.
Figure 2:
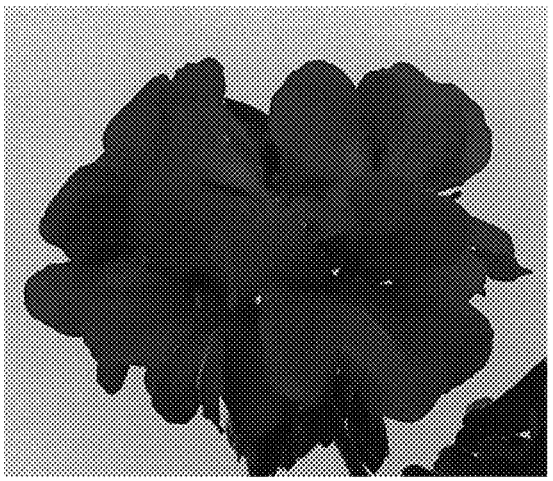
FIG. 2 illustrates a close-up view of an individual umbel of 'Tosdyndredi'.
Figure 3:
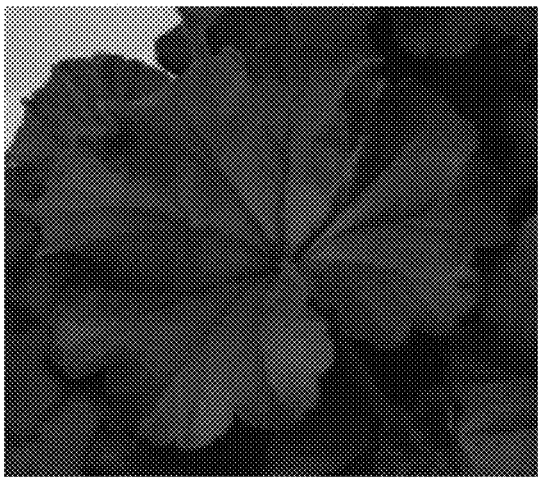
FIG. 3 illustrates a close-up view of an individual leaf of 'Tosdyndredi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in January 2020 under natural light conditions in West Chicago, Ill.

The following descriptions and measurements describe approximately 13-week-old plants produced from cuttings from stock plants and grown in a glass-covered greenhouse under conditions comparable to those used in commercial practice. The plants were grown in West Chicago, Ill. in 4.5-inch pots for approximately 9 weeks utilizing a soilless growth medium. Plants were given one pinch two weeks before transplant. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Pelargonium* Interspecific 'Tosdyndredi'.

Parentage:

*Female parent*.—Proprietary *Pelargonium* x *hortorum* breeding selection coded 17-3028, not patented.

*Male parent*.—'Xtreme Night', not patented.

Propagation:

*Type cutting*.—Terminal stem.

*Time to initiate roots*.—Approximately 9 to 12 days.

*Time to produce a rooted cutting*.—Approximately 24 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Vigorous, upright-mounded.

*Size*.—Height, from soil level to top of plant plane: Approximately 22.0 cm. Height from soil level to top of foliage: Approximately 16.0 cm. Width: Approximately 31.0 cm.

*Branching habit*.—Freely basal branching. Quantity of main branches per plant: Approximately 4.

*Branch*.—Strength: Strong. Length: Approximately 9.5 cm. Diameter: Approximately 8.0 mm. Length of central internode: Approximately 2.0 mm. Texture: Densely pubescent with a mixture of glandular and nonglandular hairs. Gland color: Colorless, transparent. Color of young and mature stem: 146C.

Foliage description:

*General description*.—Quantity of leaves per lateral branch: Approximately 8. Fragrance: Moderate. Form: Simple. Arrangement: Opposite.

*Leaves*.—Aspect: Petiole is at an acute angle to stem, blade is primarily perpendicular to stem. Shape: Reniform. Margin: Bicrenate, palmately lobed, slightly wavy. Apex: Obtuse. Base: Cordate. Venation pattern: Palmate. Length of mature leaf: Approximately 7.5 cm. Width of mature leaf: Approximately 11.5 cm. Texture of upper and lower surfaces: Densely pubescent with a mixture of glandular and nonglandular hairs. Gland color: Colorless, transparent. Color of upper surface of young foliage: Closest to 137B with a faint overlay of NN137A on zonal area, venation of 146C. Color of lower surface of young foliage: 147B with venation of 146D. Color of upper surface of mature foliage: Closest to 137A with a faint overlay of NN137A on zonal area, venation of 146C. Color of lower surface of mature foliage: Closest to 147B with venation of 146D.

*Petiole*.—Length: Approximately 8.0 cm. Diameter: Approximately 3.0 mm. Texture: Densely pubescent with a mixture of glandular and nonglandular hairs. Gland color: 17D and colorless, transparent. Color: 146B.

Flowering description:

*Flowering habit*.—'Tosdyndredi' is freely flowering under outdoor growing conditions with substantially continuous blooming from spring through autumn and year-round in greenhouse environment.

*Lastingness of individual flower on the plant*.—Approximately 12 to 14 days.

Inflorescence description:

*General description*.—Type: Umbel, semi-spherical. Positioned above foliage. Quantity of fully open umbels per plant: Approximately 2. Quantity of developing umbels per plant: Approximately: 1. Fragrance: None detected. Length or height: Approximately 6.0 cm. Width: Approximately 10.0 cm. Quantity of fully open flowers per inflorescence: Approximately 14.

*Peduncle*.—Strength: Strong. Aspect: Erect. Length: Approximately 13.0 cm. Diameter: Approximately 4.0 mm. Texture: Densely pubescent with a mixture of glandular and nonglandular hairs. Gland color: 17D and colorless, transparent. Color: 146B.

Flower description:

*General description*.—Type: Semi-double.

*Bud*.—Rate of opening: Generally takes 3 to 4 days for bud to progress from first color to fully open flower.

*Bud before opening*.—Shape: Elliptic, Length: Approximately 1.4 cm. Width: Approximately 8.0 mm. Sepal texture: Densely pubescent with a mixture of glandular and nonglandular hairs. Gland color: 17D and colorless, transparent. Petal texture: Glabrous. Petal color: 53A.

*Corolla*.—Shape: Round. Diameter: Approximately 5.0 cm. Depth: Approximately 2.0 cm.

*Petals*.—Quantity: Approximately 7 petals and 1 irregularly shaped petaloid per flower. Shape: Obovate. Appearance: Matte. Margin: Entire. Apex: Obtuse. Base: Attenuate. Length of upper petals: Approximately 3.0 cm. Width of upper petals: Approximately 2.0 cm. Length of lower petals:

Approximately 2.7 cm. Width of lower petals: Approximately 1.9 cm. Texture of upper and lower surfaces: Glabrous. Color of upper surface of upper petals when fully open: 53A to 53B with venation of 187A at base. Color of lower surface of upper petals when fully open: 53B to 53C with venation of 71B at base. Color of upper surface of lower petals when fully open: 53A to 53B. Color of lower surface of lower petals when fully open: 53C.

*Calyx*.—Shape: 5-pointed star. Diameter: Approximately 2.7 cm.

*Sepals*.—Quantity per flower: Approximately 5, fused at base. Shape: Lanceolate. Margin: Entire. Apex: Acuminate. Length of upper sepal: Approximately 1.5 cm. Width of upper sepal: Approximately 5.0 mm. Length of lower sepals: Approximately 1.2 cm. Width of lower sepals: Approximately 3.0 mm. Texture of upper surface: Glabrous. Texture of lower surface: Densely pubescent with a mixture of glandular and nonglandular hairs. Gland color: 17D and colorless, transparent. Color of upper and lower surfaces: 146D tinted with 187A at base.

*Pedicel*.—Strength: Strong. Aspect: Acute angle to peduncle. Length: Approximately 2.5 cm. Diameter: Approximately 2.0 mm. Texture: Densely pubescent with a mixture of glandular and nonglandular hairs. Gland color: 17D and colorless, transparent. Color: 1460 with a heavy overlay of 187A.

*Reproductive organs*.—Androecium: Quantity of mature stamens: Approximately 10 to 11 per flower. Anther shape: Oblong. Anther length: Approximately 2.0 mm. Anther color: 71B. Filament length: Approximately 7.0 mm. Filament color: NN155D with an overlay of 71A near anther. Pollen amount: Moderate. Pollen color: 32A. Gynoecium: Pistil quantity: 1 per flower. Pistil length: Approximately 1.0 cm. Stigma shape: 5-branched. Stigma length: Approximately 2.0 mm. Stigma color: N186D. Style length: Approximately 3.0 mm. Style color: 71A. Ovary length: Approximately 5.0 mm. Ovary texture: Densely pubescent. Ovary color: 145A.

Seed and fruit production: Neither seed nor fruit production has been observed.

Disease and pest resistance: Resistance to pathogens and pests common to Geranium has not been observed.

What is claimed is:

1. A new and distinct cultivar of Geranium plant named 'Tosdyndredi', substantially as herein illustrated and described.

* * * * *